United States Patent [19]

Haller

[11] 4,026,287
[45] May 31, 1977

[54] SYRINGE WITH RETRACTABLE CANNULA

[76] Inventor: Irene Haller, 718 Murdell Lane, Livermore, Calif. 94550

[22] Filed: Dec. 10, 1975

[21] Appl. No.: 639,264

[52] U.S. Cl. .......................... 128/215; 128/218 P
[51] Int. Cl.² ................... A61M 5/16; A61M 5/32
[58] Field of Search .............. 128/215, 216, 218 R, 128/218 P, 218 PA, 218 N, 218 NV, 221

[56] References Cited

UNITED STATES PATENTS

| | | | |
|---|---|---|---|
| 694,813 | 3/1902 | Wichester | 128/218 N |
| 2,473,733 | 6/1949 | Smith | 128/218 P |
| 2,592,381 | 4/1952 | Blackman | 128/218 P |
| 2,617,359 | 11/1952 | Van Horn | 102/92 |
| 2,722,215 | 11/1955 | Dahlgren | 128/218 |
| 2,735,428 | 2/1956 | Huber | 128/218 NV |
| 2,871,856 | 2/1959 | Steiner | 128/216 |
| 2,876,770 | 3/1959 | White | 128/215 |
| 2,887,108 | 5/1959 | Kendall | 128/218 |
| 2,972,991 | 2/1961 | Burke | 128/218 P |
| 3,151,617 | 10/1964 | Baum | 128/218 P |
| 3,306,290 | 2/1967 | Weltman | 128/218 N |
| 3,310,051 | 3/1967 | Schulte | 128/216 |
| 3,320,954 | 5/1967 | Cowley | 128/221 X |
| 3,426,448 | 2/1969 | Sarnoff | 35/17 |
| 3,678,930 | 7/1972 | Schwartz | 128/218 P |
| 3,780,734 | 12/1973 | Wulff | 128/218 R |
| 3,820,652 | 6/1974 | Thackston | 128/221 X |
| 3,828,775 | 8/1974 | Armel | 128/218 N |
| 3,889,673 | 6/1975 | Dovey et al. | 128/215 |

FOREIGN PATENTS OR APPLICATIONS 315,980  10/1969  Sweden ...................... 128/218 PA Primary Examiner—Edgar S. Burr
Assistant Examiner—Paul J. Hirsch
Attorney, Agent, or Firm—Phillips, Moore, Weissenberger, Lempio & Majestic

[57] ABSTRACT

A syringe having a barrel and a piston actuated plunger reciprocable therein includes a means for retracting the cannula subsequent to dispensing fluid from the syringe. The plunger is engageable with the forward end wall of the syringe barrel after the fluid is dispensed so that retraction of the plunger causes the end wall to break away from the barrel and retract the cannula attached thereto entirely within the barrel. In this manner, accidental puncture and contamination by the cannula is avoided. A plurality of serrations on the forward end wall and adjacent its juncture with the syringe barrel allows the forward end wall to be broken away after mating surfaces on the forward end wall and the plunger rod are engaged. In a first embodiment, the mating surfaces are threaded so that rotation of the plunger rod is required for engagement. In a second embodiment, rotation is not required since the mating surfaces are in the form of a snap-in annular rib and groove. An annular rib is also provided at the open end of the barrel to prevent unwanted retraction of the plunger from the barrel.

9 Claims, 8 Drawing Figures

U.S. Patent  May 31, 1977  4,026,287
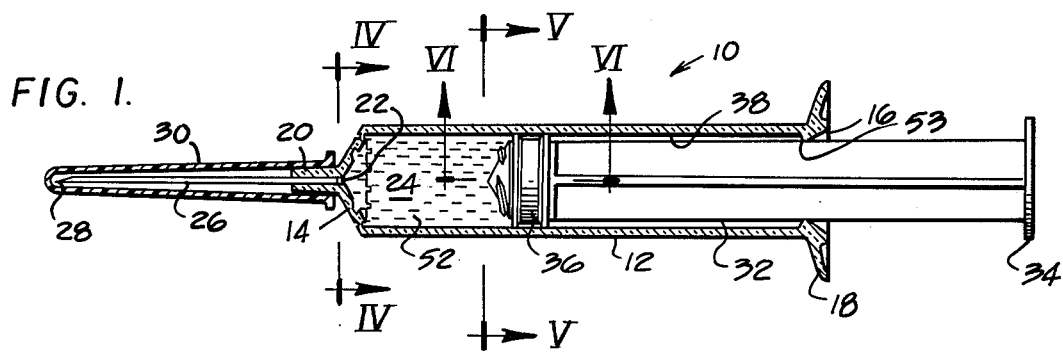
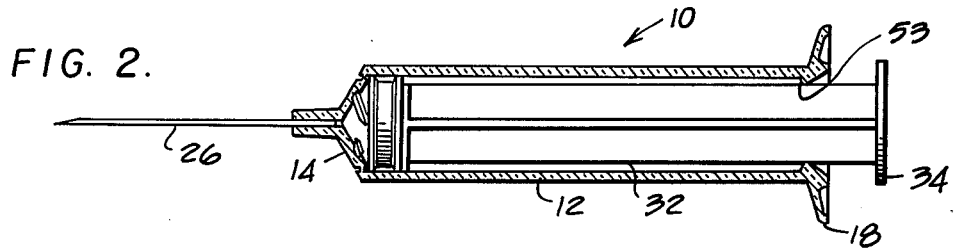
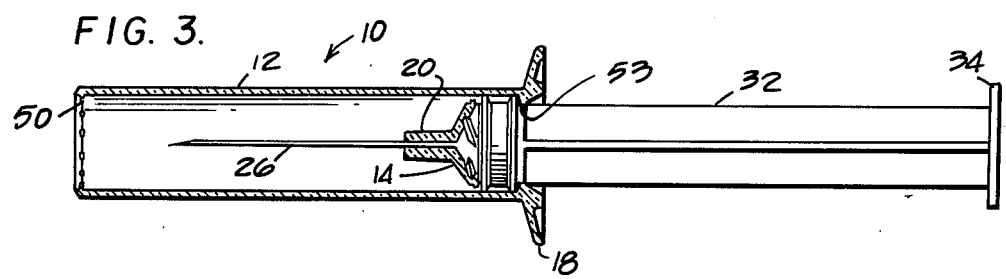
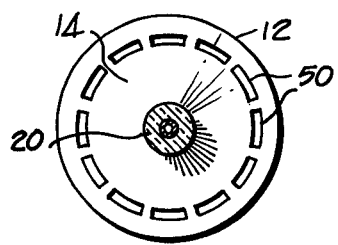
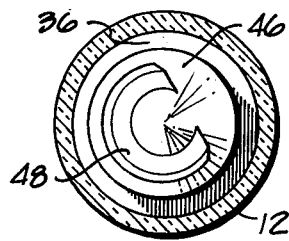
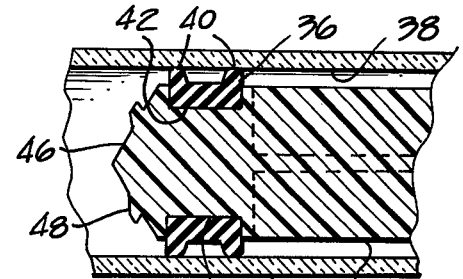
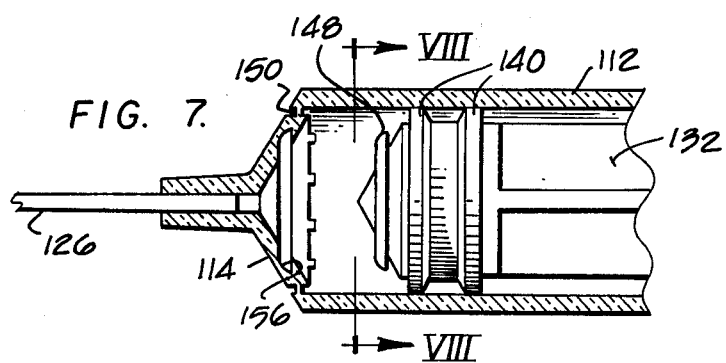
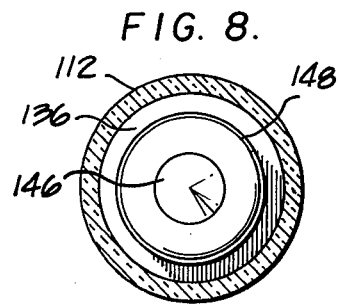

SYRINGE WITH RETRACTABLE CANNULA

BACKGROUND OF THE INVENTION

This invention relates to a syringe having a rectractable cannula. More particularly, this invention relates to a hypodermic syringe which may be used for administering serum, antibiotics, or the like, and in which the sharp pointed cannula thereof is retractable subsequent to injection to avoid contamination and injury.

Current hypodermic syringes present a problem in that the sharp-pointed cannula thereof frequently causes injury and infection subsequent to the administration of the medicinal fluid contained within the syringe. Typically, a hypodermic syringe is used in the form of a disposable, preloaded syringe of plastic material having a barrel and a piston reciprocable by means of a plunger therein. A sharp-pointed cannula is fixed to the forward end wall of the syringe barrel and is protected by means of a removable plastic sheath. A difficulty is encountered subsequent to injection of the fluid when the protective sheath is attempted to be replaced over the cannula. Frequently, the person administering the injection inadvertently becomes stuck by the now-contaminated cannula. This can cause the spread of various diseases, including hepatitis. In any event, it is costly to hospitals and other medical facilities in terms of time and administration costs. Typically, an incident report has to be filled out for each such inadvertent wounding. In addition, a hepatitis shot may have to be given to the person so wounded.

SUMMARY AND OBJECTS OF THE INVENTION

It is therefore the primary object of this invention to provide an improved hypodermic syringe having a retractable cannula.

It is a further object of this invention to provide such a syringe having a cannula which is retractable entirely within the body of the syringe subsequent to expulsion of the syringe fluid.

It is a further object of this invention to provide such a syringe in which retraction of the cannula is accomplished automatically upon retraction of the plunger subsequent to expulsion of the fluid.

It is a further object of this invention to provide such a syringe wherein complete retraction of the piston therefrom is prevented.

The invention takes the form of a hypodermic syringe having a hollow, generally tubular barrel with a forward end wall closing the forward end and, an open rear end. An annular rib is provided in the rear end for preventing complete removal of a reciprocable piston contained therein. The tubular reciprocable piston is a generally annular resilient rubber member which has a bore therethrough. The bore contains a plunger rod which may be of harder plastic material. One end of the plunger rod extends out of the barrel end in the conventional fashion. The other end of the plunger rod extends forwardly of the piston.

Further and other objects of this invention will become more readily apparent from a review of the following description and attached drawing.

BRIEF DESCRIPTION OF THE DRAWING

FIG. 1 is a front elevational sectional view of a syringe of the instant invention shown prior to injection of the fluid contained therein;

FIG. 2 is a view of the same shown after injection of fluid has been completed and prior to retraction of the cannula;

FIG. 3 is a view of the same after retraction of the cannula fully into the syringe barrel;

FIG. 4 is a view taken along lines IV—IV in FIG. 1 and illustrating details of the barrel end wall;

FIG. 5 is a view taken along lines V—V in FIG. 1 and showing details of the means for engaging the forward end wall;

FIG. 6 is a cross sectional view taken along lines VI—VI in FIG. 1 showing details of the piston and plunger rod;

FIG. 7 is a view similar to FIG. 6 showing details of a second embodiment of the engagement means; and FIG. 8 is a view taken along lines VIII—VIII in FIG. 7, further illustrating the same.

DETAILED DESCRIPTION

Turning now to FIG. 1, there is shown generally at 10 a disposable syringe of the instant invention which comprises a generally tubular hollow barrel 12 of plastic material. The plastic may conveniently be clear for viewing of its contents. A tapered forward end wall 14 closes the forward end of the barrel while the rear of the barrel is open as at 16. An annular rib 18 is formed around the rear open end of the barrel 16 to provide a place for gripping by the operator's fingers. Projecting from the forward end wall 14 is a tapered mounting post 20 having a passage 22 axially positioned therein leading from the barrel shape of 24 to the exterior of the syringe. Within passage 22 is fixedly mounted a cannula 26 having a sharp-pointed end 28. In order to protect the cannula from contamination as well as unwanted puncturing of the operator, a tapered hollow sheath 30 is fitted over post 20. This tapered hollow sheath may be removed prior to injection to expose the sharp-pointed cannula 26. Projecting from the rear end of the syringe barrel is a plunger rod 32 of generally cruciform shape in cross section and having a flat planar thumb surface 34 at the rear end thereof and mounting a resilient annular piston 36 at the forward end thereof which is in reciprocable sealing engagement with the syringe barrel interior 38.

As seen in FIG. 6, the plunger rod may be of plastic material with the annular piston of rubber material. As there seen, annular piston 36 has a pair of spaced annular sealing ridges 40 therearound. Piston 36 has a bore 42 therethrough so that the piston may be fitted within an accommodating groove 44 at the front end of plunger rod 32. As seen, the front end of plunger rod 32 projects forwardly of piston 36 and has a conical tapered surface 46 thereon. Turning to FIG. 5, the conical tapered surface also includes an engaging means in the form of a thread 48 for selective engagement with the barrel end wall as will be more fully described hereinafter.

As best seen in FIG. 4, forward end wall 14 includes a circumferentially oriented plurality of serrations 50 adjacent the juncture of the end wall of barrel 12. The purpose of these serrations is to allow the end wall to be selectively broken away from the barrel.

In operation, an injection is given to dispense fluid 52 through the cannula upon advance of the plunger rod 32 towards the forward end of the syringe barrel. As seen in FIG. 2, when the plunger rod is fully advanced and rotated, thread 48 engages in an accommodated threaded recess 54 in end wall 14. As seen in FIG. 3, the retraction of plunger 32 causes end wall to break away along flangable serrations 50 so as to allow cannula 26 to be withdrawn entirely within barrel 12. In this manner, the cannula is fully protected within the syringe barrel. An annular stop 53 at the open end 16 of the barrel prevents the entire removal of rod 32 from the barrel.

Turning to FIGS. 7 and 8, there is shown an alternate embodiment of the invention which eliminates the necessity of rotating the rod to positively engage the front end wall 114. With this embodiment the mating surfaces are in the form of an annular rib 148 engageable within an accommodating annular groove 156 in forward end wall 114. The plastic material of rib 148 is slightly deformable and shaped with a ramp shaped forward portion and flat rear portion so that it may be easily engaged in the forward direction and resist disengagement in the rearward direction of motion of plunger 132. In this manner, the frangible serrations 150 are easily broken away when the plunger rod is retracted.

It will be obvious from the preceding description that other modifications are possible within the scope of the present invention as defined by the following appended claims.

What is claimed is:

1. In a hypodermic syringe having a hollow barrel having an end wall closing said barrel at the forward end of said syringe, and an open rear end; a piston means in reciprocable sealing engagement with the interior of said barrel defining a chamber in said barrel for containing fluid; a cannula mounted on said end wall defining an interior passage; and an aperture in said end wall communicating said cannula interior passage with said chamber, the improvement which comprises means for rectracting said cannula entirely within said chamber subsequent to reciprocation of said piston means to discharge said fluid from said chamber so that accidental injury is avoided, said means for retracting comprising frangible means for enabling separation of said forward wall from said barrel, and engagement means for selectively attaching said piston means to said forward end wall whereby retracting of said piston means toward said rear end after attaching said piston means to said end wall causes breaking of said frangible means and the retraction of said cannula into said barrel.

2. The invention of claim 1 wherein said cannula has a sharp pointed end to facilitate puncture.

3. The invention of claim 1 wherein said attaching means comprises mating surfaces on said piston means and end wall.

4. The invention of claim 3 wherein said mating surfaces are in the form of thread means so that turning of said piston causes engagement or disengagement of said thread means.

5. The invention of claim 3 wherein said mating surfaces are in the form of an annular rib and groove.

6. The invention of claim 1 wherein said frangible means comprise serrations in said end wall at the juncture with said barrel.

7. The invention of claim 1 further including stop means in said barrel adjacent the open end for limiting retraction of said piston means from said barrel.

8. The invention of claim 1 wherein said piston means comprises an annular resilient piston defining a piston bore therethrough and a plunger rod fitted in said piston bore, a portion of said plunger rod extending beyond opposite ends of said piston into said chamber and beyond said open rear end.

9. The invention of claim 8 wherein said means for retraction comprises mating surfaces on said chamber portion of said plunger rod and said end wall.

* * * * *